United States Patent
Cao et al.

(10) Patent No.: US 6,589,389 B2
(45) Date of Patent: Jul. 8, 2003

(54) TEST METHOD FOR DETERMINING BLEED-THROUGHS IN OLD CORRUGATED CONTAINER FIBER PULP

(75) Inventors: Bangji Cao, Appleton, WI (US); Oliver U. Heise, Menasha, WI (US)

(73) Assignee: Voith Paper, Inc., Appleton, WI (US)

( * ) Notice: Subject to any disclaimer, the term of this patent is extended or adjusted under 35 U.S.C. 154(b) by 0 days.

(21) Appl. No.: 09/964,244

(22) Filed: Sep. 26, 2001

(65) Prior Publication Data

US 2003/0056909 A1 Mar. 27, 2003

(51) Int. Cl.[7] .............. D21C 5/02; G01N 33/34
(52) U.S. Cl. ............ 162/198; 162/4; 162/DIG. 4; 162/49; 73/53.03
(58) Field of Search ............. 162/4–8, 48, 49, 162/71, 72, 198, 199, 263, 272, DIG. 4, 55, 56, 162; 73/53.03, 54.43, 61.72

(56) References Cited

U.S. PATENT DOCUMENTS

| | | | |
|---|---|---|---|
| 4,326,912 A | 4/1982 | Mollett | 162/5 |
| 5,131,980 A | 7/1992 | Chamblee et al. | 162/4 |
| 5,302,245 A | 4/1994 | Nadeau | 162/8 |
| 5,377,844 A | 1/1995 | Hwang | 209/167 |
| 5,540,814 A * | 7/1996 | Curtis et al. | 162/181.8 |
| 5,597,447 A * | 1/1997 | Hank et al. | 162/135 |
| 5,639,346 A | 6/1997 | Marwah et al. | 162/5 |
| 5,707,489 A | 1/1998 | Von Grumbkow et al. | 162/4 |
| 5,718,801 A * | 2/1998 | Li et al. | 162/4 |
| 5,744,043 A | 4/1998 | Cutts et al. | 210/705 |
| 5,817,212 A * | 10/1998 | Jobbins et al. | 162/4 |
| 5,855,769 A | 1/1999 | Firth et al. | 209/164 |
| 5,985,095 A | 11/1999 | Scholz | 162/5 |

FOREIGN PATENT DOCUMENTS

EP    0 632 158 A1    6/1994 ........... D21C/5/02

* cited by examiner

*Primary Examiner*—Peter Chin
*Assistant Examiner*—Eric Hug
(74) *Attorney, Agent, or Firm*—Taylor & Aust, P.C.

(57) ABSTRACT

A test method for analyzing an OCC fiber pulp, to quantify the content therein of contaminants creating bleed-throughs in a paper product formed from the pulp. A sample of the pulp is formed into a sheet, and bleed-throughs are created from the contaminants therein by hot-pressing the sheet. A dye is applied to the sheet, to enhance contrast between areas of the sheet having bleed-throughs and areas of the sheet not having bleed-throughs. The contrasted sheet is analyzed to determine the quantity of contaminants that create bleed-throughs.

11 Claims, 1 Drawing Sheet

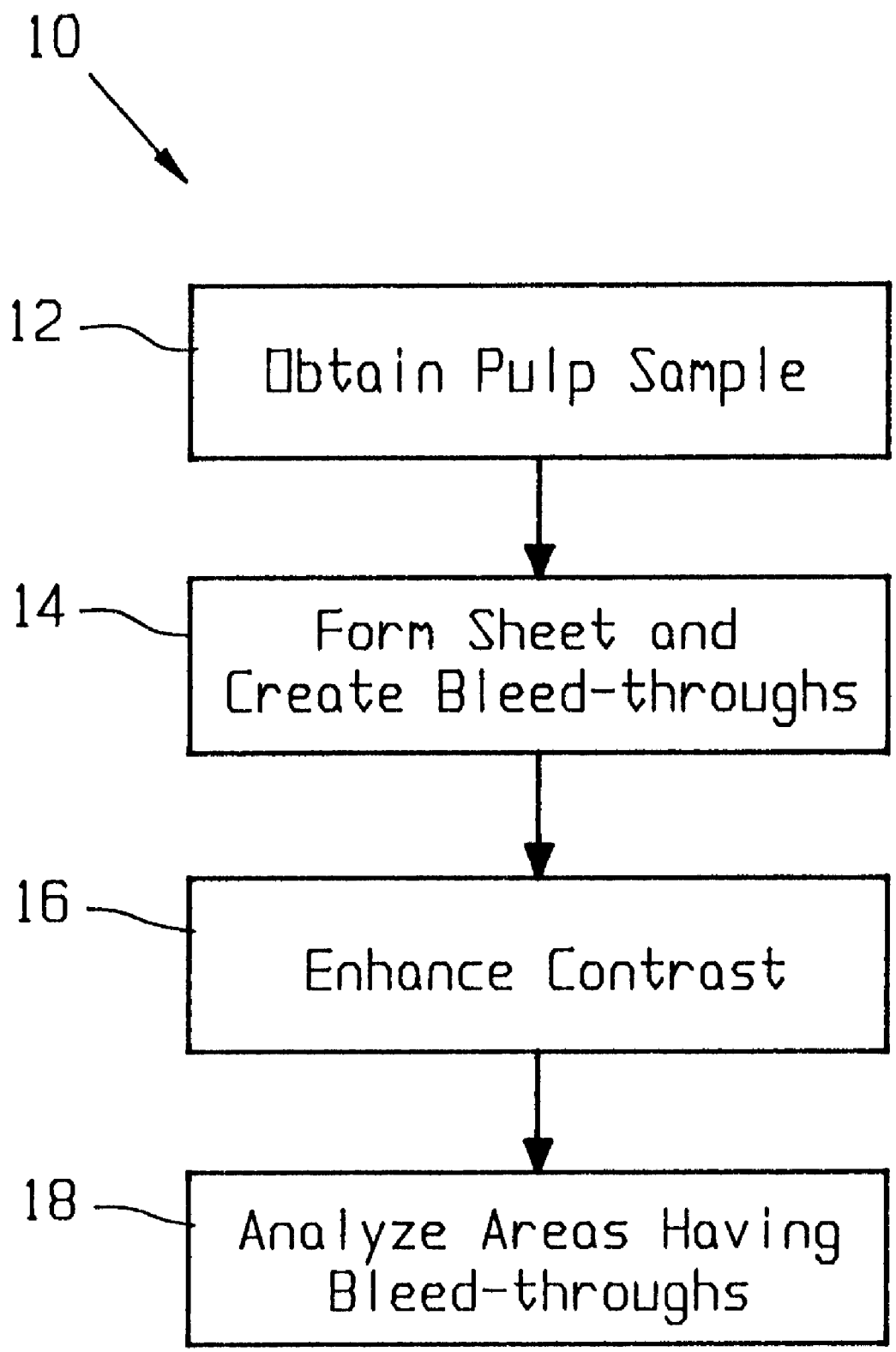

TEST METHOD FOR DETERMINING BLEED-THROUGHS IN OLD CORRUGATED CONTAINER FIBER PULP

BACKGROUND OF THE INVENTION

1. Field of the Invention

The present invention relates to a method for testing pulp samples used to make paper products, and, more particularly, to a test method for determining the amount of contaminants that would create bleed-throughs in a product manufactured from the pulp.

2. Description of the Related Art

The use of old corrugated container (OCC) for making new containerboard increased rapidly in the 1980s and early 1990s. According to American Forest and Paper Association, the recycling rate of OCC, defined as the ratio of the tonnage of OCC grade fiber used at paper and paperboard mills to that of total containerboard supply, increased from 39.5% in 1987 to 63.4% in 1996. Since then, the recycling rate has stabilized at about 63.5%.

At such high recycling rates, removal of contaminants from OCC becomes crucial to assure quality standards of the products made from OCC fiber. Standard processes to recycle OCC consist of a pulper, detrasher, high-density cleaner, coarse screen, forward cleaner, fine screen, reverse or through-flow cleaner and a thickener. Although the majority of large contaminants can be removed by such a processing sequence, many fine contaminant particles remain in the processed pulp. These fine particles may either be brought in by the contaminated OCC, or generated by the fragmentation of larger particles during the treatment process. Tests on samples of fine screen accepts indicate that the size of the fine contaminants ranges from 80 $\mu$m to 750 $\mu$m in equivalent diameter, with an average of about 170 $\mu$m. Therefore, the majority of the fine contaminants can pass easily through a 0.20 mm (200 $\mu$m) slotted screen basket, which is the type of basket used in most OCC recycle mill fine screen systems. Many large particles also are able to pass through the screen baskets, due to the shape or flexibility of the particle. Reverse and through-flow cleaners have also proven to be ineffective in removing these contaminants, since the specific density of "bleed-throughs" are close to 1, and the size of the contaminant is too small to create sufficient drag forces to differentiate the contaminant from pulp fibers.

Failure in removing the fine contaminants, together with the increasing usage of OCC, has caused a growing deterioration in the qualities of recycled pulp. One of the greatest concerns regarding pulp quality is the formation of objectionable "bleed-throughs" in dried paperboard. "Bleed-throughs" are formed from the melting of fine contaminants. At the elevated temperature (approximately 350° F.) of a papermaking machine dryer section, many of the fine contaminants will melt and migrate into voids of the fiber web. At the spot occupied by a melted contaminant, a dark bleed-through is formed, which gives the finished paperboard an objectionable appearance. The concentration of "bleed-throughs" in paper sheets, tested with an image analyzer, can reach as high as 50,000 ppm, that is, 5% of the total sheet area is covered with dark "bleed-throughs". The "bleed-throughs" also can cause problems in converting operations, such as brown tissue embossing and the making of gypsum-board.

The worst situation occurs in mills using 100% recycled fiber. In these mills, each time the OCC is recycled, more contaminants are brought in to the fiber stream. The contaminants accumulate with each recycling of the fiber, and eventually the pulp becomes unsuitable for making new paper products because of the high concentration of contaminants.

Methods have been proposed for more efficient removal of small contaminants that form "bleed-throughs" in the final products. One such method is disclosed in our co-pending application, U.S. Ser. No. 09/800,031 filed Mar. 6, 2001, now U.S. Pat. No. 6,425,982, entitled, "System and Method For Removing Bleed-Throughs From Old Corrugated Container Fiber Pulp."

A problem in processing OCC pulp by any process is determining the level of contamination in the pulp by contaminant particles that would result in "bleed-throughs" in a final product. It is advantageous in processing such a pulp to know the level of contamination in the pulp, and to evaluate the effectiveness of the process for removing the contaminants. It is also desirable to have a reliable test method for testing the contaminant level at the inlet and the outlet of equipment in the removal process, so that the efficiency of the equipment, for the pulp being processed, can be evaluated. Since many of the contaminants are small, and often not readily apparent in the pulp until after manufacture of the product, known testing procedures are often ineffective in determining the level of contamination in the pulp. Often the level of contamination is low, and the sources of the contamination are complex and ever changing. The particles are small, and difficult to remove from the fibers.

What is needed in the art is a test method for determining in OCC pulp the level of contamination by particles that would form "bleed-throughs" in the final product.

SUMMARY OF THE INVENTION

The present invention provides a test method for determining the level of "bleed throughs" contamination in OCC fiber pulp, including forming a sheet of the pulp to create the "bleed-throughs", dying the pulp fibers to enhance the contrast between the "bleed-throughs" and the fiber, and analyzing the sample with an image analyzer.

The invention comprises, in one form thereof, a test method for measuring the bleedthrough contaminant content of a fiber pulp. The method steps include obtaining a sample of the pulp; forming a paper web from the sample of the pulp; drying the web to form a sheet; melting the bleed-through contaminants in the sheet; enhancing the contrast between areas of the sheet having bleed-through contaminants and areas of the sheet not having bleed-through contaminants; and analyzing the contrasted sheet for ascertaining the concentration of bleed-throughs in the sheet.

The invention comprises, in another form thereof, a test method for analyzing an old corrugated container fiber pulp, to evaluate the content therein of contaminants creating bleed-throughs in a paper product formed from the pulp. The test method includes steps of obtaining a sample of the OCC pulp; forming a handsheet from the sample; heating the handsheet to create bleed-throughs from the contaminants in the handsheet; enhancing contrast between regions of the handsheet having bleed-through contaminants and regions of the handsheet not having bleed-through contaminants; and analyzing the enhanced handsheet to determine the concentration of bleed-throughs in the sheet.

The invention comprises, in a further from thereof, a test method for analyzing an old corrugated container fiber pulp, to evaluate the content therein of contaminants creating bleed-throughs in a paper product formed from the pulp. The test method includes steps of obtaining a sample of the pulp; forming a paper sheet from the sample, including creating bleed-throughs from the contaminants contained in the sheet, enhancing contrast between regions of the sheet having bleed-throughs and regions of the sheet not having bleed-throughs; and analyzing the enhanced sheet to determine the determine the concentration of bleed-throughs in the sheet.

An advantage of the present invention is that the amount of fine contaminants in a pulp sample, which cause bleed-through flaws in a fiber web, is determined accurately.

Another advantage is that the test method simulates a paper forming process, to more accurately evaluate the level of contamination by contaminants that would actually form "bleed-throughs".

A further advantage is that the test method of the present invention uses standard pulp and paper testing procedures, and equipment commonly found in pulp and paper testing laboratories, and does not-require investment in expensive equipment not useful for other testing purposes.

BRIEF DESCRIPTION OF THE DRAWINGS

The above-mentioned and other features and advantages of this invention, and the manner of attaining them, will become more apparent, and the invention will be better understood by reference to the following description of an embodiment of the invention, taken in conjunction with the accompanying drawing, which is a flow diagram of an embodiment of the present invention for a test method for determining the amount of bleed-through contaminants in OCC fiber pulp. The exemplification set out herein illustrates one preferred embodiment of the invention, in one form, and such exemplification is not to be construed as limiting the scope of the invention in any manner.

DETAILED DESCRIPTION OF THE INVENTION

Referring now to the drawing, there is shown a test method 10 according to the present invention, for analyzing a fiber pulp, such as recycled old corrugated container (OCC) pulp. Test method 10 provides an accurate, easily performable test method to determine the level of contamination in the pulp by contaminants that likely would create bleed-throughs in a product formed from the pulp.

Test method 10 according to the present invention can be used to analyze untreated pulp, to determine the level of contamination in the pulp before the pulp is subjected to a process for removing contaminants that would lead to bleed-throughs. Test method 10 also can be used to analyze the effectiveness of various stages in a contaminant removal process, or the effectiveness of the entire process for removing such contaminants. When used at intermediate stages of a contaminant removal process, the test method will analyze small contaminants that may be created from larger contaminants in process steps that precede testing. With this information, earlier steps in the process can be modified to reduce the creation of small contaminants from larger ones, or subsequent steps can be modified to enhance contaminant removal efficiencies.

Test method 10 includes a first step 12 of obtaining a sample of the pulp. The sample can be obtained using known sampling techniques, and step 12 may include the taking of numerous samples at different times. The individual samples thus obtained can be treated individually in the test method to be described, or several small samples can be batched to obtain an "average" sample of the pulp at a given time. Samples can be obtained from several different locations along the removal process, to evaluate performance of equipment or stages within the process, as will be described hereinafter.

In a step 14, the pulp sample is formed into a sheet while creating bleed-throughs from the contaminants in the pulp. Various known procedures can be used to form a web of the pulp and to dry the web to form a sheet. An efficient and repeatable procedure for consistency in testing is desirable. Forming handsheets according to the testing standards of the Technical Association of the Pulp and Paper Industry (TAPPI) is appropriate. In forming the handsheet, a sample of the pulp is pressed between two platens, under pressure of between about 8 psi and about 16 psi. The basis weight of the handsheet should be about 60 $g/m^2$, ±3 $g/m^2$. To create the bleed-throughs in the handsheet, one or both platens are heated to between about 280° F. and about 360° F. The handsheet is held under pressure between the heated platens for about 10 minutes, which causes fine contaminants in the sheet to melt and diffuse into the sheet, creating bleed-throughs. Hot-pressing in this manner simulates formation on a papermaking machine, and the temperatures found in papermaking machine dryer section, which would create bleed-throughs from the contaminants in the pulp.

Bleed-throughs in a handsheet of OCC pulp generally appear as darker spots in the somewhat lighter background of the OCC sheet. The bleed-throughs may be semi-transparent, and thus somewhat difficult to see against the background of a sheet made from OCC fiber pulp.

In a step 16, the contrast is enhanced, between regions of the handsheet having bleed-throughs and regions of the sheet not having bleed-throughs, to facilitate subsequent analysis of the sheet in a step 18.

In step 16, the handsheet is dyed in a water-soluble black ink to enhance the contrast between bleed-throughs and sheet background. Since the cellulosic fibers are highly hydrophilic, areas of the handsheet that have no bleed-throughs will readily absorb a water-based pigment solution. Thus, if, for example, a water-soluble black ink is used, the cellulosic fibers absorb the ink, and become black. On the other hand, the bleed-throughs are hydrophobic, and repel water-based pigment solutions. A water-soluble black ink is not absorbed by the bleed-throughs, and the bleed-throughs remain undyed. The contrast between regions of the handsheet having bleed-throughs and regions of the handsheet not having bleed-throughs is thereby enhanced.

In preparation for step 18, the dyed handsheet is allowed to air-dried.

Analysis of the handsheet in-step 18 is performed to determine the contaminant level of the pulp forming the handsheet. An image analyzer is used to evaluate the contaminant level. Such devices are known in the paper recycling industry, and have the capacity to detect light contraries according to the lightness or darkness. With the dye enhanced hand sheet from step 16, the contaminant level can be quantified readily in step 18, and is expressed in terms of contaminant parts-per-million (ppm) of the sheet area.

Test method 10, practiced according to the invention, can be used to calculate the removal efficiency of individual process components, or of the total system. In evaluating the efficiency a machine, for example, samples are obtained from the feed stock flow to the machine, and from the accepts stock flow from the machine. Each sample is processed according to the test method of the present invention, to ascertain the contaminant level of the sample, expressed as "ppm". Handsheets are formed using hot-pressing techniques, so that bleed-throughs are created in the handsheet. The handsheets are dyed to enhance the contrast between regions of the handsheet having bleed-throughs and regions of the handsheet not having bleed-throughs. The handsheets are then evaluated by an image analyzer, so that a contaminant level, expressed in ppm, is obtained for each the feed and accepts samples. The machine efficiency is expressed as a removal efficiency percentage. The reduction in contaminants is compared to the inlet contaminant level according to the following formula:

$$E = \frac{C_{feed} - C_{accepts}}{C_{feed}} \times 100$$

Where:
E is the removal efficiency of the machine expressed in %.
$C_{feed}$ is the feed sample bleed-through contaminant level, expressed as ppm.
$C_{accepts}$ is the accepts sample bleed-through contaminant level, expressed as ppm.

The present invention provides an accurate test method for determining the bleed-through contaminant level in a pulp stock, such as OCC. The process includes sheet formation from a sample of the stock, and creation of bleed-throughs from the contaminants. The hydrophilic qualities of the fibers in the stock and the hydrophobic characteristics of the bleed-throughs are taken advantage of to selectively dye the fibers with water-based ink. Subsequent analysis of the sheet with an image analyzer yields an accurate calculation of the level of contamination with bleed-through contaminants. Since actual bleed-throughs are created, and subsequently are evaluated, the test method accurately reflects the contaminant level. The test method is relatively easy to perform, and is thereby easily repeatable. Known pulp and paper testing techniques and equipment are used, and the test method can be practiced without significant specialized training or additional investment.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A test method for measuring the bleedthrough contaminant content of a fiber pulp, comprising:
    obtaining a sample of the pulp;
    forming a paper web from the sample of the pulp;
    applying heat to the web within a range from about 280° F. to about 360° F.;
    pressing the web within a range from about 8 psi to about 16 psi;
    drying the web to form a sheet;
    melting the bleed-through contaminants;
    enhancing the contrast between areas of the sheet having bleed-through contaminants and areas of the sheet not having bleed-through contaminants; and
    analyzing the contrasted sheet for quantifying the level of contamination with contaminants that produce bleed-throughs.

2. The method of claim 1, said drying and melting steps performed by pressing the web with a heated platen.

3. The method of claim 1, said step of enhancing the contrast performed by applying a water-soluble dye to the sheet.

4. The method of claim 3, including air-drying the dyed sheet.

5. The method of claim 4, said step of analyzing the contrasted sheet performed with an image analyzer.

6. The method of claim 1, including air-drying the contrast enhanced sheet.

7. The method of claim 1, said step of analyzing the contrast enhanced sheet performed with an image analyzer.

8. A test method for analyzing an old corrugated container fiber pulp, to evaluate the content therein of contaminants creating bleed-throughs in a paper product formed from the pulp, said test method comprising:
    obtaining a sample of old corrugated container pulp;
    forming a handsheet from the pulp sample;
    applying heat to the handsheet within a range from about 280° F. to about 360° F.; and
    pressing the handsheet within a range from about 8 psi to about 16 psi; to create bleed-throughs from the contaminants in the handsheet;
    enhancing contrast between regions of the handsheet having bleed-through contaminants and regions of the handsheet not having bleed-through contaminants; and
    analyzing the contrasted sheet for quantifying the level of contamination with contaminants that would produce bleed-throughs.

9. The test method of claim 8, said step of enhancing contrast between regions of the handsheet having bleed-through contaminants and regions of the handsheet not having bleed-through contaminants performed by applying a water-soluble dye to the handsheet.

10. A test method for analyzing an old corrugated container fiber pulp, to evaluate the content therein of contaminants creating bleed-throughs in a paper product formed from the pulp, said test method comprising:
    obtaining a sample of old corrugated container pulp;
    forming a paper sheet from the sample, including creating bleed-throughs from the contaminants contained in the pulp;
    enhancing contrast between regions of the sheet having bleed-throughs and regions of the sheet not having bleed-throughs; and
    analyzing the enhanced sheet to determine the percentage area of the sheet having bleed-throughs.

11. The test method of claim 10, said step of enhancing contrast between regions of the sheet having bleed-throughs and regions of the sheet not having bleed-throughs including applying a water-soluble dye to the sheet.

* * * * *